United States Patent
Sutradhar

(10) Patent No.: US 6,946,572 B2
(45) Date of Patent: Sep. 20, 2005

(54) CRYSTALLIZATION OF ADIPIC ACID FROM ITS SOLUTION IN AQUEOUS NITRIC ACID

(75) Inventor: Bhagya Chandra Sutradhar, Wilmington, DE (US)

(73) Assignee: Invista North America S.a.r.l., Wilmington, DE (US)

( * ) Notice: Subject to any disclaimer, the term of this patent is extended or adjusted under 35 U.S.C. 154(b) by 119 days.

(21) Appl. No.: 10/687,167

(22) Filed: Oct. 16, 2003

(65) Prior Publication Data

US 2005/0085666 A1 Apr. 21, 2005

(51) Int. Cl.$^7$ .............................................. C07C 51/42
(52) U.S. Cl. ...................................................... 562/593
(58) Field of Search ................................. 562/593, 543, 562/590

(56) References Cited

U.S. PATENT DOCUMENTS 3,096,369 A * 7/1963 Soeterbroek et al. ....... 562/593
4,254,283 A * 3/1981 Mock ......................... 562/530

* cited by examiner

Primary Examiner—Paul A. Zucker

(57) ABSTRACT

Process for crystallization of adipic acid from a nitric acid oxidation product of cyclohexane in which process the oxidation product is subject to crystallization in a series of crystallizers of decreasing crystallization temperature.

3 Claims, 2 Drawing Sheets

CRYSTALLIZATION OF ADIPIC ACID FROM ITS SOLUTION IN AQUEOUS NITRIC ACID

FIELD OF THE INVENTION

The invention relates to crystallization of adipic acid from its solution in aqueous nitric acid and especially to the recovery of adipic acid from the product of oxidation of cyclohexanol and cyclohexanone by aqueous nitric acid

BACKGROUND OF THE INVENTION

Adipic acid is commercially produced by the oxidation of cyclohexanol and cyclohexanone by concentrated nitric acid. Initial product recovery and purification are accomplished through crystallization of the reaction mixture followed by solid-liquid separation. Additional purification of adipic acid is accomplished through one or more steps of aqueous recrystallization followed by solid-liquid separation. The reaction of cyclohexanol and cyclohexanone with nitric acid produces adipic acid with several byproducts, e.g. glutaric acid, succinic acid, of varying concentrations. In order to produce adipic acid of good quality, a major part of the purification needs to be accomplished during the initial product recovery through crystallization of the reaction mixture from the nitric acid oxidation step.

For crystallization of adipic acid from the solution obtained from the oxidation of cyclohexanol and cyclohexanone by nitric acid, it has generally been observed that the higher the temperature of crystallization, the purer the product of crystallization. However, the mother liquor from crystallization at high temperature contains a high concentration of adipic acid. In order to prevent loss of adipic acid with the mother liquor of crystallization, most refining processes in commercial practice require that this crystallization be conducted at a low temperature, typically below 60 degrees C. As a result, the product obtained contains substantial impurity that requires significant additional refining. It would, therefore, be beneficial to have a process to achieve the benefit of high temperature crystallization without excessive product loss in the mother liquor.

SUMMARY OF THE INVENTION

In the present invention, the crystallization is conducted in a plurality of crystallization stages in decreasing order of operating temperature beginning with a first crystallizer and ending with a final crystallizer. Each crystallizer is operated in a continuous mode of operation. A feed solution is introduced in the first crystallizer and a product slurry is withdrawn from the final crystallizer. The temperature of the first crystallizer should be such that it is significantly higher than the temperature of the final crystallizer, yet a substantial concentration of solid particles is achieved in the first crystallizer in order to alleviate the detrimental effect of low solids concentration in the first stage crystallizer.

The present invention, therefore, is a process for the crystallization of an adipic acid-containing oxidation product produced by the nitric acid oxidation of cyclohexanone (K) and cyclohexanol (A), said oxidation product comprising adipic acid, glutaric acid and nitric acid, said process comprising, introducing into a first crystallizer said oxidation product, said crystallizer providing a first crystallization temperature sufficient to produce a first crystallizer product comprising a first mother liquor and a first harvest of solid crystals, said solid crystals being present at a concentration of at least about 10 weight percent based on the combined weight of the mother liquor and the crystals;

introducing the first crystallizer product into a second crystallizer providing a second crystallizer temperature lower than said first temperature to produce a second crystallizer product comprising a second mother liquor and a second harvest of solid crystals, said second mother liquor having a lower concentration of adipic acid than said first mother liquor and said second harvest of solid crystals having a greater weight percent of adipic acid than said first harvest; and either harvesting the solid crystals from the second crystallizer if the concentration of adipic acid in solution in the second mother liquor is less than or equal to a pre-selected concentration in the range of about 2 to 12 weight percent of the weight of the second mother liquor, or, if the concentration of adipic acid in solution in the second mother liquor is higher than said pre-selected concentration in the range of about 2 to 12 weight percent of the weight of the second mother liquor, then introducing the second crystallizer product into one additional crystallizer or a plurality of additional crystallizers in series providing successively lower crystallization temperatures until a final crystallization product comprising a final mother liquor and a final harvest of solid crystals is produced in which the concentration of adipic acid in solution in the final mother liquor is less than or equal to said pre-selected concentration in the range of about 2 to 12 weight percent of the weight of the final mother liquor, and harvesting the solid crystals from the final crystallization product.

BRIEF DESCRIPTION OF THE DRAWING

The drawing consists of three figures.

DETAILED DESCRIPTION OF THE INVENTION

Figure 1:
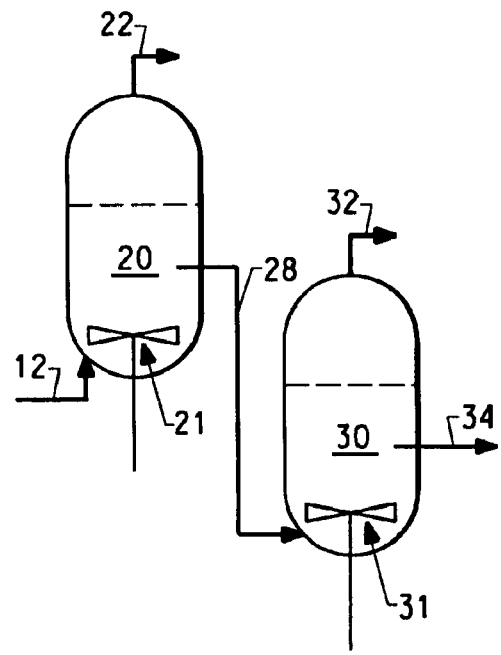
FIG. 1 depicts a block diagram of a process embodying the present invention involving only two stages in the crystallization process.

Referring now to FIG. 1, there is shown a block diagram illustrating apparatus that embodies one embodiment of the present invention involving only two stages in the crystallization process, namely, a first crystallizer and a second crystallizer.

An adipic acid-containing oxidation product (12) produced by the nitric acid oxidation of cyclohexanone (K) and cyclohexanol (A) is continuously fed into a first crystallizer (20). In the first crystallizer, the oxidation product is cooled down to a first crystallization temperature. The cooling action causes crystallization of adipic acid in solution in the oxidation product that is fed to the first crystallizer to produce a first crystallizer product comprising a first mother liquor and a first harvest of solid crystals. The first crystallization temperature should be low enough to allow enough adipic acid in solution in the oxidation product to crystallize so that the concentration of solid crystals in the first crystallizer is at least about 10 weight percent based on the combined weight of the mother liquor and the crystals in the first crystallizer. A portion of the first crystallizer product (28) is continuously withdrawn from the first crystallizer and fed to a second crystallizer (30).

The first crystallizer product is further cooled down in the second crystallizer to a second crystallization temperature. Cooling action in the second crystallizer causes crystallization of adipic acid in solution in the first mother liquor associated with the first crystallizer product that is fed to the second crystallizer to produce a second crystallizer product comprising a second mother liquor and a second harvest of solid crystals. The second crystallization temperature is selected in a way that the concentration of adipic acid in solution in the second mother liquor is less than the concentration of adipic acid in solution in the first mother liquor and is less than or equal to a pre-selected concentration in the range of about 2 to 12 weight percent of the weight of the second mother liquor. The concentration of solid crystals in the second crystallizer product is, therefore, higher than the concentration of solid crystals in the first crystallizer product. A portion of the second crystallizer product (34) is continuously withdrawn from the second crystallizer and is processed through a solid-liquid separation unit (not shown) to harvest the solid crystals.

If the concentration of adipic acid in solution in the second mother liquor is higher than said pre-selected concentration, the second crystallizer product stream (34) can be fed to a final crystallizer or to a plurality of additional crystallizers in series ending in a final crystallizer (not shown) and providing successively lower crystallization temperatures until a final crystallization product comprising a final mother liquor and a final harvest of solid crystals is produced. The final crystallization temperature should be selected in a way that the concentration of adipic acid in solution in the final mother liquor is less than the concentration of adipic acid in solution in any preceding stage mother liquor and is less than or equal to said pre-selected concentration in the range of about 2 to 12 weight percent of the weight of the final mother liquor. The concentration of solid crystals in the final crystallizer product is, therefore, higher than the concentration of solid crystals in any preceding crystallizer product. A portion of the final crystallizer product (not shown) is continuously withdrawn from the final crystallizer and is processed through a solid-liquid separation unit (not shown) to harvest the solid crystals.

Generally it is not advantageous to use more than three stages of crystallization and in many cases two stages of crystallization provides adequate benefit.

The oxidation mixture is generally hot and unsaturated, typically containing about 15 to 25% adipic acid and typically at a temperature in the range of about 75 to 95 degrees C. Typically about 25 to 45% nitric acid, about 5 to 15 wt % glutaric acid and about 2 to 10 wt % succinic acid are present in the oxidation product. On the basis of combined weight of water and nitric acid only, the concentration of nitric acid should be in the range of about 45 to 55 wt %.

The first crystallizer is an enclosed vessel in which a constant volume of the first crystallizer product should be maintained. It is equipped with an agitation device (21) in order to keep a uniform suspension of solids in the mother liquor in the entire crystallizer. Optionally, a draft tube (not shown) can be installed inside the crystallizer. Cooling is generally accomplished by evaporating at a sub-atmospheric pressure a portion the water and nitric acid (i.e. the solvent) contained in the oxidation product. A continuous flow of vapor (22) leaves the top of the crystallizer.

The concentration of solids in the first crystallizer should be at least 10 wt % based on the total weight of the first crystallizer product. A high solids concentration is beneficial for crystallizer operation and for purity of final product. The concentration of solids in the first crystallizer can be increased by increasing the concentration of adipic acid in the oxidation product fed to the first crystallizer, decreasing the first crystallizer temperature, introducing solid adipic acid crystals, e.g. from a second crystallizer product, operating the first crystallizer in a double draw-off (DDO) mode. In the DDO mode of operation, a stream of crystallizer content, called overflow, comprising preferentially small particles is withdrawn simultaneously with a stream of crystallizer content, called underflow, comprising particles of all sizes. This action increases concentration of solid particles in the crystallizer.

The first crystallizer can be a single vessel or multiple vessels in parallel (not shown). A residence time of about 15 to 150 minutes (based on the total flow rate of the oxidation product fed to the first crystallizer) should be allowed for the first crystallizer (for each vessel if multiple vessels in parallel are used). In order to prevent flashing of any solvent, there should be adequate liquid height above the location at which the oxidation product is introduced in the crystallizer and there should be adequate mixing.

The second crystallizer is an enclosed vessel in which a constant volume of the second crystallizer product should be maintained. It is equipped with an agitation device (31) in order to keep a uniform suspension of solids in the mother liquor in the entire crystallizer. Optionally, a draft tube (not shown) can be installed inside the crystallizer. Cooling is generally accomplished by evaporating at a sub-atmospheric pressure a portion of the water and nitric acid (i.e. solvent) contained in the first crystallizer product. A continuous flow of vapor (32) leaves the top of the crystallizer. A portion of the second crystallizer product (34) is continuously withdrawn from the second crystallizer.

The concentration of solids in the second crystallizer product is greater than the concentration of solids in the first crystallizer product, i.e. greater than about 10 wt % based on the total weight of the second crystallizer product. The second crystallizer temperature should be in the range of about 30 to 60 degrees C. The concentration of adipic acid in the second mother liquor should be in the range of about 2 to 12 wt %.

The second crystallizer can be a single vessel or multiple vessels in parallel (not shown). A residence time of about 15 to 150 minutes (based on the total flow rate of the first crystallizer product fed to the second crystallizer) should be allowed for the second crystallizer (for each vessel if multiple vessels in parallel are used). In order to prevent flashing of any solvent, there should be adequate liquid height above the location at which the first crystallizer product is introduced in the crystallizer and there should be adequate mixing.

The third or any subsequent stage crystallizer can be designed and operated in a way similar to the second crystallizer as described above. The preselected concentration of dissolved adipic acid for the second or any subsequent mother liquor is based on the value that is acceptable for further processing, e.g., recycling the mother liquor.

Figure 2:
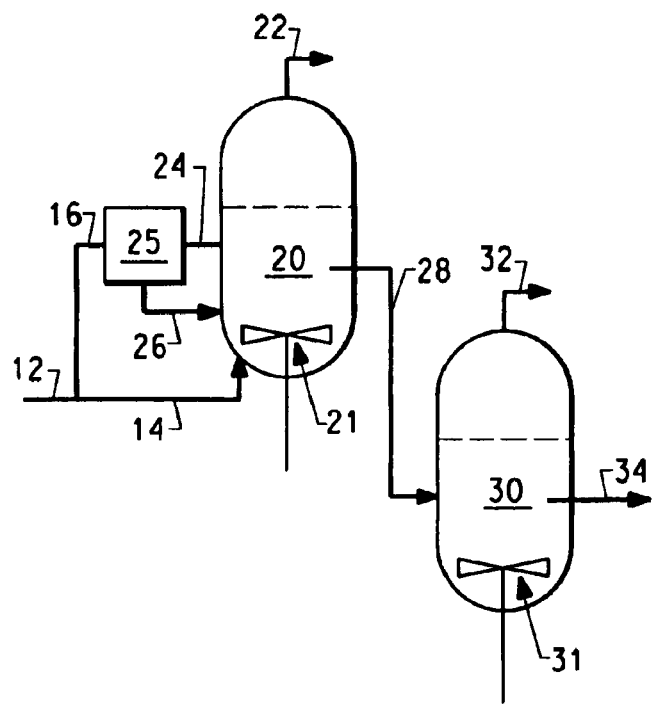
FIG. 2 depicts a block diagram of one embodiment of the present invention in which at least a portion of an adipic acid-containing oxidation product is premixed with a first crystallizer product and then introduced into the first crystallizer.

Referring now to FIG. 2, there is shown a block diagram illustrating apparatus that embodies an embodiment of the present invention in which at least a portion of the adipic acid-containing oxidation product is premixed with at least a portion of the first crystallizer product and then introduced into the first crystallizer. In this embodiment of the invention, the flow of adipic acid-containing oxidation product (12) is split into two parts (14) and (16). Stream (14) is directly fed into the first crystallizer. Stream (16) is fed into a first feed pre-mixer vessel (25) where it combines with a flow (24) of the first crystallizer product. A first premixed feed (26) of the above combined streams is withdrawn from the first pre-mixer vessel and fed into the first crystallizer.

The first pre-mixer vessel can be a small, enclosed tank or a section of a pipe or an isolated zone inside the crystallizer. It can be operated liquid full and should be designed to accomplish intimate mixing of the streams. It should be advantageous to combine the streams in such a ratio that the liquor after mixing is slightly unsaturated. For example, 100 g of oxidation product containing about 20 wt % adipic acid, about 5wt % glutaric acid about 5 wt % succinic acid, about 35 wt % nitric acid and about 35 wt % water at 92 degrees C. and 100 g of mother liquor obtained from first crystallizer product at 60 degrees C. containing about 12 wt % adipic acid, about 5 wt % glutaric acid about 5 wt % succinic acid, about 39 wt % nitric acid and about 39 wt % water will produce a significantly unsaturated liquor upon mixing intimately.

Together with an unsaturation in liquor, an adequate residence time should be provided so that at least a portion of the fine particles of adipic acid might dissolve. For example, for a mixture temperature of about 50 to 75 degrees C., a residence time of about 1 to 5 minutes should be adequate. Optionally, heat can be provided in order to accomplish dissolving of fine particles.

Figure 3:
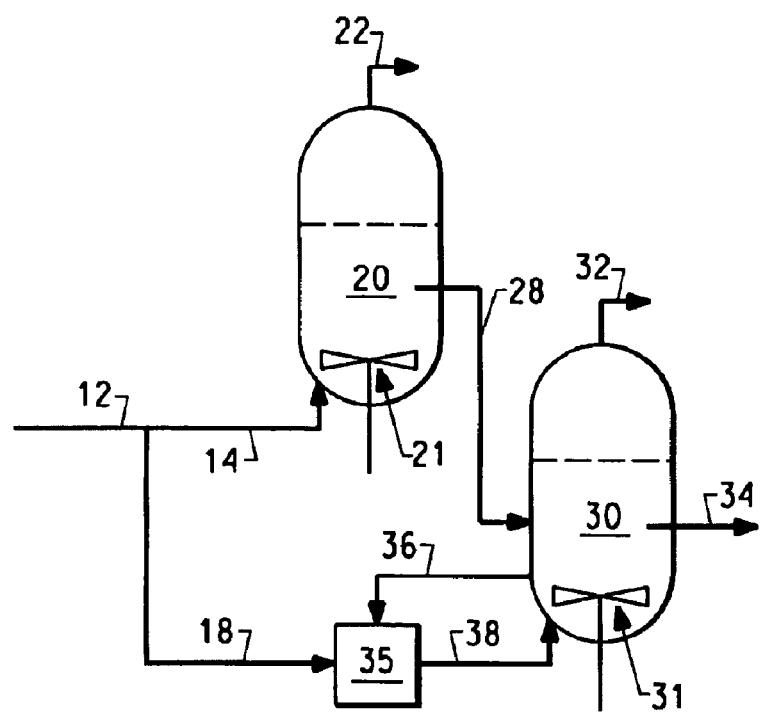
FIG. 3 shows a block diagram of another embodiment of the present invention in which at least a portion of an adipic acid-containing oxidation product is premixed with a second crystallizer product and then introduced into the second crystallizer.

Referring now to FIG. 3, there is shown a block diagram illustrating apparatus that embodies another embodiment of the present invention in which at least a portion of the adipic acid-containing oxidation product is premixed with at least a portion of the second crystallizer product and then introduced into the second crystallizer. In this embodiment of the invention, the flow of adipic acid-containing oxidation product (12) is split into two parts (14) and (18). Stream (14) is directly fed into the first crystallizer. Stream (18) is fed into a second feed pre-mixer vessel (35) where it combines with a flow (36) of the second crystallizer product. A second premixed feed (38) of the above combined streams is withdrawn from the second pre-mixer vessel and fed into the second crystallizer.

The second pre-mixer vessel can be a small, enclosed tank or a section of a pipe or an isolated zone inside the crystallizer. It can be operated liquid full and should be designed to accomplish intimate mixing of the streams. It should be advantageous to combine the streams in such a ratio that the liquor after mixing is slightly unsaturated. In addition, an adequate residence time should be provided so that at least a portion of the fine particles of adipic acid might dissolve. For example, for a mixture temperature of about 50 to 75 degrees C., a residence time of about 1 to 5minutes should be adequate. Optionally, heat can be provided in order to accomplish dissolving of fine particles.

It may be beneficial to have an arrangement in which at least a portion of the adipic acid oxidation product is premixed with at least a portion of any crystallizer product from a crystallizer subsequent to the second crystallizer and then introduced into the same crystallizer.

What is claimed is:

1. A process for the crystallization of adipic acid from an adipic acid-containing oxidation product produced by the nitric acid oxidation of cyclohexanone and cyclohexanol, said oxidation product comprising adipic acid, glutaric acid, water and nitric acid, said process comprising, introducing into a first crystallizer said oxidation product, said crystallizer providing a first crystallization temperature sufficient to produce a first crystallizer product comprising a first mother liquor and a first harvest of solid adipic acid crystals, said solid adipic acid crystals being present at a concentration of at least about 10 weight percent based on the combined weight of the mother liquor and the crystals;

introducing the first crystallizer product into a second crystallizer providing a second crystallizer temperature lower than said first temperature to produce a second crystallizer product comprising a second mother liquor and a second harvest of solid adipic acid crystals, said second mother liquor having a lower concentration of adipic acid than said first mother liquor and said second crystallizer product having a greater weight percent of solid adipic acid crystals than said first crystallizer product; and either harvesting the solid adipic acid crystals from the second crystallizer product if the concentration of adipic acid in solution in the second mother liquor is less than or equal to a pre-selected concentration in the range of about 2 to 12 weight percent of the weight of the second mother liquor, or, if the concentration of adipic acid in solution in the second mother liquor is higher than said pre-selected concentration in the range of about 2 to 12 weight percent of the weight of the second mother liquor, then introducing the second crystallizer product into one additional crystallizer or a plurality of additional crystallizers in series providing successively lower crystallization temperatures until a final crystallization product comprising a final mother liquor and a final harvest of solid adipic acid crystals is produced in which the concentration of adipic acid In solution in the final mother liquor is less than or equal to said pre-selected concentration in the range of about 2 to 12 weight percent of the weight of the final mother liquor, and harvesting the solid adipic acid crystals from the final crystallization product;

wherein at least a part of cooling in the crystallizers is accomplished by evaporating at a sub-atmospheric pressure a portion of water and nitric acid.

2. The process of claim 1 further comprising
(a) withdrawing at least a portion of the first crystallizer product from the first crystallizer,
(b) combining at least a portion of the adipic acid-containing oxidation product and the first crystallizer product from step (a) to produce a first premixed feed slurry, and
(c) feeding the first premixed feed slurry to the first crystallizer.

3. The process of claim 1 further comprising
(a) withdrawing at least a portion of the second crystallizer product from the second crystallizer,
(b) combining at least a portion of the adipic acid-containing oxidation product and the crystallizer product from step (a) to produce a second premixed feed slurry, and
(c) feeding the second premixed feed slurry to the second crystallizer.

* * * * *